United States Patent [19]

Dive et al.

[11] Patent Number: 5,389,612
[45] Date of Patent: Feb. 14, 1995

[54] PHOSPHONIC PEPTIDE INHIBITORS OF BACTERIAL COLLAGENASES

[75] Inventors: Vincent Dive, Vincennes; Flavio Toma, Clamart, both of France; Athanasios Yiotakis, Athens, Greece

[73] Assignee: Commissariat a l'Energie Atomique, France

[21] Appl. No.: 949,760

[22] Filed: Sep. 23, 1992

Related U.S. Application Data

[63] Continuation of Ser. No. 613,123, Nov. 15, 1990, abandoned.

[30] Foreign Application Priority Data

Nov. 15, 1989 [FR] France ............... 89 14978

[51] Int. Cl.$^6$ ............ A61K 37/64; A61K 37/02; C07K 5/08; C07K 5/10
[52] U.S. Cl. .................. 514/7; 514/18; 514/19; 530/331; 530/332
[58] Field of Search ........... 514/7, 18, 19; 530/331, 530/332

[56] References Cited

U.S. PATENT DOCUMENTS

| | | | |
|---|---|---|---|
| 4,472,381 | 9/1984 | Sakakibara et al. | 530/331 |
| 4,558,034 | 12/1985 | Galardy et al. | 514/7 |
| 4,935,404 | 6/1990 | Hunter et al. | 514/7 |
| 5,100,874 | 3/1992 | Odake et al. | 514/18 |

FOREIGN PATENT DOCUMENTS

0085488 10/1983 European Pat. Off. .

OTHER PUBLICATIONS

Seifter et al, "The Collagenases", pp. 670–677 in *The Enzymes*, vol. III, 3rd Edition, Boyer (Academic Press 1971).
"Phosphorus–containing Inhibitors of Angiotensin–converting Enzyme", Thorsett et al., Proc. Natl. Acad. Sci. USA, vol. 79, pp. 2176–2180, Apr. 1982.
"Inhibition of Collagenase from *Clostridium Histolyticm* by Phosphoric and Phosphonic Amides", Galardy et al., Biochemistry 1983, vol. 22, pp. 4556–4561.
Eur. J. Biochem. 172, 761–766, 1988. New Thiol Inhibitors of *Clostridium Histolyticum* Collagenase, Yiotakis et al.
Eur. J. Biochem., 191, pp. 685–693, 1990. Inhibition of *Chlostridium Histolyticum* Collagenases by Phosphonamide Peptide Inhibitors, Dive et al.

*Primary Examiner*—Stephen G. Walsh
*Attorney, Agent, or Firm*—Hayes, Soloway, Hennessey, Grossman & Hage

[57] ABSTRACT

The invention relates to novel derivatives of peptides usable as inhibitors of bacterial collagenases.

These derivatives comply with the formula:

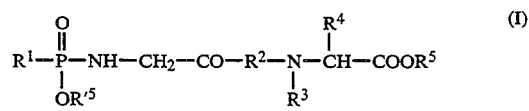

in which $R^1$ is an optionally substituted aryl or aralkyl group or the group

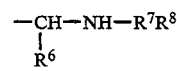

with $R^6$ being the side chain of an α-amino acid and $R^7R^8$ a protective group or a radical derived from an amino acid or a protected peptide, $R^2$ is derived from proline, hydroxyproline, thiazolidine or dehydroproline, $R^3$ is H or an alkyl, and $R^4$ is the side chain of an amino acid and $R^5$ and $R'^5$ are H, a metal, an alkyl or benzyl.

The derivatives in which $R'^5$ is a metal or hydrogen can be used as inhibitors of bacterial collagenases.

17 Claims, No Drawings

PHOSPHONIC PEPTIDE INHIBITORS OF BACTERIAL COLLAGENASES

This is a continuation of application(s) Ser. No. 07/613,123, filed on Nov. 15, 1990, now abandoned.

The present invention relates to novel derivatives of peptides usable as inhibitors of bacterial collagenases and belonging to the class of zinc metalloproteases.

More specifically, it relates to derivatives of polypeptides having a phosphonamide chelating group able to interact strongly with the zinc atom of the active site of said collagenases.

Collagen is a majority component of the extracellular matrix of pluricellular eukaryotic organisms. Thus, it is the main constituent of the skin, tendons, bones, cartilages and tissues and represents approximately 40% of all the proteins of the human body.

Although the collagen molecule is very resistant to the action of most proteases, it is still degraded by proteases specific thereto, namely collagenases.

Two distinct classes of collagenases have hitherto been identified and are characterized by the specificity of the cuts which they bring about in the collagen molecule. The first collagenase class is constituted by collagenases of higher organisms, which hydrolyze the peptide bonds containing the Gly-Ile or Gly-Leu pair, whereas the second class is constituted by bacterial collagenases, which systematically hydrolyze all the peptide bonds having the sequence X-Gly and in general degrade all the collagen molecule.

Bacterial collagenases belong to the class of zinc metalloproteases and the existence of a zinc atom in their catalytic site directly involved in the hydrolysis reaction of the peptide bond of the substrates, makes it possible to develop competitive inhibitors of these enzymes. These inhibitors, which can be derivatives of peptides, have a peptide part, whose function is to effect specific interactions with the bonding subsites of the enzyme, as well as a chelating group able to strongly interact with the zinc atom of the active site.

This enzyme-substrate interaction model specific to the group of zinc proteases has recently made it possible to develop powerful inhibitors having interesting pharmacological properties. Reference can be made among these to encephalinases and inhibitors of the conversion enzyme, e.g. those described by Thorserf et 81 in Proc. Natl. Acad. Sci. USA. vol.79, 1982, pp.2176-2180. However, these compounds only have a very weak activity with respect to bacterial collagenases. This is explained by the fact that each of these three zinc proteases (encephalinase, conversion enzyme and bacterial collagenase) has a different specificity.

In the case of bacterial collagenases, recent works have shown that it was possible, on the basis of the hypotheses developed hereinbefore, also to produce for said class of proteases pseudo-peptide inhibitors having a chelating group, namely thiol, ketone or phosphoramide.

Thus, Yotakis et al in Eur. J. Biochem, vol.160, pp.413–418, 1986 and in Eur. J. Biochem., vol.172, pp.761–766, 1988, have demonstrated that the compounds HS-CH$_2$-CH$_2$-CO-Pro-Arg and HS-CH$_2$-CH$_2$-CO-Pro-Har inhibited collagenases produced by *Achromobacter iophagus* and *Clostridium histolyticum*, the inhibition constants Ki obtained being $400 \cdot 10^{-9}$ and $210 \cdot 10^{-9}$M.

Galardy et al in Biochemistry, vol.22, no.19, pp.4556–4561, 1983 and in U.S. Pat. No. 4,558,034 demonstrated that dipeptides and tripeptides having a phosphoryl group inhibited the collagenase of *Clostridium histolyticum*. In this case, for the best isoamyl compound -PO$_2$Gly-Pro-Ala, the inhibition constant Ki is $20 \cdot 10^{-6}$M, but these peptides are not specific for the collagenase, because they are more powerful inhibitors of the conversion enzyme.

Mookhtiar et al in Biochemistry, vol.27, pp.4299–4304, 1988 showed that peptide derivatives having a ketone function could inhibit *Clostridium histolyticum* collagenases. In this case, the inhibition constant Ki is $1 \cdot 10^{-6}$M for the best compound (cinnamoyl - Leuk-Gly-Pro-Arg).

Thus, none of the known inhibitors leads to inhibition constants of approximately 1 nanomole.

Research has been continued for the purpose of finding other more active inhibitors and particularly in the group of inhibitors having a phosphoryl group, The interest of such compounds is that they represent perfect analogs of the transition state of the collagenase substrates and are therefore able to very strongly interact with the enzyme.

Moreover, unlike in the case of compounds having a thiol group, these compounds permit modifications on either side of the phosphoryl group, thus permitting a better investigation of the factors governing both the activity and the selectivity of the compounds.

The present invention specifically relates to novel derivatives of peptides, which are more powerful inhibitors of bacterial collagenases than the presently known inhibitors.

According to the invention, these derivatives of peptides comply with the formula:

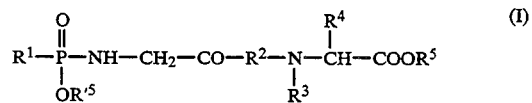

in which R$^1$ represents a group chosen from among aryl and aralkyl groups either not substituted or substituted on their aryl part by at least one substituent chosen from among the halo, trifluoromethyl, C$_1$-C$_4$ alkoxy, C$_1$-C$_4$ alkyl, C$_1$-C$_4$ alkanoyloxy, C$_2$-C$_5$ carbonyloxyalkyl, nitro, carboxy or cyano groups and the group of formula:

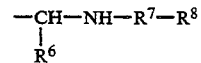

in which R$^6$ is the side chain of an α-amino acid, R$^7$ is a single bond or a radical derived from an α-amino acid or a peptide of formula:

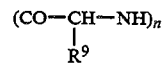

in which R$^9$ is the side chain of an α-amino acid, n is an integer from 1 to 2 and R$^9$ can differ when n>1, linked to NH by CO; and R$^8$ is a group blocking the N termination of an α-amino acid or an aralkyl group either not substituted or substituted by at least one substituent chosen from among the halo, trifluoromethyl, C$_1$-C$_4$ alkoxy, C$_1$-C$_4$ alkyl, C$_{1-C4}$ alkanoyloxy, C$_2$-C$_5$ carbonyloxyalkyl, nitro, carboxy or cyano groups; $R^2$ is a divalent radical derived from an α-amino acid chosen from among proline, hydroxyproline, thiazolidine and dehydroproline of formulas:

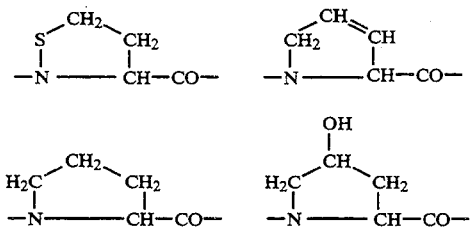

connected by its NH part to CO, $R^3$ is a hydrogen atom or a $C_1$–$C_4$ alkyl group, $R^4$ is a $C_1$–$C_5$ alkyl group or the side chain of an α-amino acid and $R^5$ and $R'^5$, which can be the same or different, are a hydrogen atom, a metal, a $C_1$–$C_5$ alkyl group or a benzyl group, provided that $R^1$ has a hydrogen atom and $R^4$ the n-butyl group when $R^1$ is an unsubstituted aryl or aralkyl group.

In these derivatives of peptides, the choice of $R^1$ makes it possible to obtain more powerful inhibitors than those obtained by Galardy, in which the groups used corresponding to $R^1$ are alkyl, e.g. ethyl or isoamyl groups.

Thus, by using according to the invention an aryl or aralkyl group and preferably an aralkyl group substituted on its aryl part, there is an improvement to the interaction between $R^1$ and the subsite $P_1$ of the collagenase, which makes it possible to obtain more powerful inhibitors, whose activity can in particular be regulated by appropriately choosing the alkyl group and the type of substituent introduced onto the aryl part.

The inhibiting power of the derivatives of peptides is also improved by placing after the phosphoryl group, a group of type:

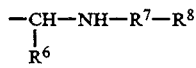

having one or two amino acid analogs. Thus, in this case, the groups substituting the phosphorus atom are amino acids and are consequently very close to the structure of a collagenase type substrate in the transition state.

The term "aryl" used here covers systems having a heretocyclic and carbocyclic aromatic nucleus containing e.g. one or more heteroatoms, such as O, S and N. These aryl groups generally have 3 to 10 carbon atoms. Examples of aryl groups are phenyl, naphthyl, furyl, thienyl, pyrolyl, imidazolyl, pyridyl, pyrimidinyl, indolyl, quinolyl, oxazolyl and isooxazolyl groups.

The term "aralkyl" here designates groups formed by the association of an aryl group and an alkyl group. These aryl groups can be of the type described hereinbefore. The alkyl groups can be straight or branched and preferably have 1 to 4 carbon atoms.

According to the invention, the aralkyl group can be substituted on its aryl part by at least one substituent chosen from among the halo groups, e.g. fluorine, chlorine, bromine or iodine, trifluoromethyl, $C_1$–$C_4$ alkoxy, $C_1$–$C_4$ alkyl, $C_1$–$C_4$ alkanoyloxy, carbonyloxyalkyl with a $C_1$–$C_4$ alkyl group, nitro, carboxy and cyano.

According to the invention, when $R^1$ represents an aryl group, it can also be substituted by the aforementioned groups.

The term "α-amino acid" used here relates to 20 α-amino acids commonly found in proteins and which are known under the name of standard amino acids and their analogs. The side chains of these amino acids comprise straight and branched alkyl groups, hydroxyalkyl, carboxyalkyl, aralkyl, aminoalkyl, carboxamide alkyl, mercapto alkyl, phenyl alkyl, hydroxyphenyl alkyl, guanidino alkyl, imidazoyl alkyl, indolyl alkyl and pyrrolidinyl.

Examples of amino acids which can be used are alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenyl alanine, homoarginine, thiazolidine and dehydroproline.

The expression "group blocking the N termination of an α-amino acid" covers all blocking groups usable for blocking the amino functions of amino acids and peptides, e.g. t-butoxycarbonyl, benzyloxycarbonyl, cinnamoyl, pivaloyl and N-(9-fluorenyl-methoxycarbonyl) groups.

The metals usable for $R^5$ and $R'^5$ are in particular pharmaceutically acceptable metals, e.g. alkali metals such as sodium and lithium.

According to a first embodiment of the invention, $R^1$ is a group chosen from among aryl and aralkyl groups, either unsubstituted or substituted on their aryl part by at least one substituent chosen from among halo, trifluorornethyl, $C_1$–$C_4$ alkoxy, $C_1$–$C_4$ alkyl, $C_1$–$C_4$ alkanoyloxy, $C_2$–$C_5$ carbonyloxy alkyl, nitro, carboxy or cyano groups.

According to a first variant of this embodiment, $R^1$ is an unsubstituted aryl or aralkyl group and in this case $R^3$ is a hydrogen atom and $R^1$ the n-butyl group.

Examples of such derivatives are those complying with formula I, in which $R^1$ is the phenyl ethyl or phenyl methyl group.

According to a second preferred variant of said first embodiment of the invention, $R^1$ is an aryl or aralkyl group substituted on its aryl part by at least one of the substituents described hereinbefore. Examples of such groups are nitrophenyl ethyl and trifluorornethyl phenyl ethyl groups.

In this preferred variant $R^3$ and $R^4$ can be of different types. Thus, the extremity

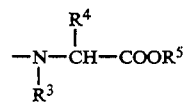

of the peptide derivative can correspond to different amino acids. For example, it can be norleucine and in this case $R^3$ is a hydrogen atom and $R^4$ is n-butyl.

In these two variants of the first embodiment of the invention, $R^2$ is derived from an amino acid chosen from among proline, hydroxyproline, thiazolidine and dehydroproline. Thus, $R^2$ can comply with the following formulas:

$$\begin{array}{cc} \text{H}_2\text{C}\overset{\text{CH}_2}{\diagup}\text{CH}_2 & \text{H}_2\text{C}\overset{\overset{\text{OH}}{|}}{\underset{|}{\text{CH}}}\text{CH}_2 \\ -\text{N}\underset{}{\longrightarrow}\text{CH}-\text{CO}, & -\text{N}\underset{}{\longrightarrow}\text{CH}-\text{CO}- \\ \text{S}\overset{\text{CH}_2}{\diagup}\text{CH}_2 & \text{H}_2\text{C}\overset{\text{CH}}{\diagdown}\text{CH} \\ -\text{N}\underset{}{\longrightarrow}\text{CH}-\text{CO}- & -\text{N}\underset{}{\longrightarrow}\text{CH}-\text{CO}- \end{array}$$

Preferably, $R^2$ is the proline derivative and complies with the formula:

$$-\text{N}\underset{}{\longrightarrow}\text{CH}-\text{CO}-$$

In these two variants of the first inventive embodiment, $R^5$ and $R'^5$ can be a hydrogen or metal atom, or an alkyl or benzyl group. The metal can e.g. be lithium or sodium.

The alkyl groups used, which can be straight or branched, preferably have 1 to 4 carbon atoms.

According to a second embodiment of the invention, $R^1$ is the group of formula:

$$-\underset{\underset{R^6}{|}}{\text{CH}}-\text{NH}-R^7-R^8-$$

In this case, $R^6$ is the side chain of an amino acid, e.g. a methyl, benzyl or isobutyl group.

$R^7$ can be a single bond or a radical derived from an amino acid or a peptide. Numerous amino acids can be used for adapting the structure of the derivative to the enzyme to be inhibited. For example $R^7$ can be the radical derived from proline of formula:

$$-\text{CO}-\text{CH}\underset{}{\longrightarrow}\text{N}-$$

In this second embodiment of the invention, $R^8$ is a group blocking the N termination of an α-amino acid, e.g. the benzyloxy carbonyl group. $R^8$ can also be an optionally substituted aryl or aralkyl group, such as those described hereinbefore for the first embodiment.

In this second embodiment of the invention, $R^2$, $R^3$, $R^4$, $R^5$ and $R'^5$ can be constituted by different groups or atoms described hereinbefore for the first inventive embodiment. Thus, $R^2$ can be derived from proline, $R^3$ and $R^4$ can correspond to norleucine, $R^5$ can be H, Li, Na or the benzyl group and $R'^5$ can be H, Li or Na.

In this second embodiment of the invention, it is thus possible to choose $R^6$ and $R^7$ in such a way as to have on the other side of the phosphoryl group other amino acids and to improve the selectivity of the peptide derivative with respect to other zinc metalloproteases.

With respect to bacterial collagenases, these peptide derivatives have a different kinetic behaviour from that of the derivatives according to the first inventive embodiment. Thus, they are very slowly fixed to the active site of the enzyme, but have very long residence times on the active site and the halflife of the complex can e.g. be 12 to 25 hours. Thus, they are characterized by a very limited action reversibility. Moreover, their bond to the enzyme cannot be displaced by an excess of substrate of the enzyme, which is very important for a pharmacological action. This is of interest for pharmaceutical applications, because the complex formed with the target enzyme cannot be destabilized by an enzyme substrate excess. Moreover, these peptide derivatives do not inhibit the conversion enzyme.

The peptide derivatives according to the invention can be prepared by conventional processes like that described by ThorseLf et al in Proc. Natl. Aced. Sci. USA. vol.79, pp.2176-2180, 1982.

Thus, the derivatives corresponding to the first embodiment of the invention can be prepared by a process having the following successive stages:

a) Synthesis of a Dibenzyl Phosphonate of Formula:

$$R^1-\underset{\underset{O}{\|}}{P}-(OCH_2-C_6H_5)_2 \qquad (II)$$

according to the following reaction diagram:

$$(C_6H_5-CH_2-O-)_2\overset{\overset{O}{\|}}{P}-H + Na^+H^- \longrightarrow$$

$$(C_6H_5-CH_2O)_2\overset{\overset{O}{\|}}{P}-Na^+ + H_2$$

$$(C_6H_5CH_2O-)_2\overset{\overset{O}{\|}}{P}-Na^+ + R^1Br \longrightarrow$$

$$(C_6H_5-CH_2O-)_2\overset{\overset{O}{\|}}{P}-R^1 + NaBr$$

b) Synthesis of the Benzyl Phosphonate Chloride of Formula:

$$C_6H_5-CH_2O-\underset{\underset{R^1}{|}}{\overset{\overset{O}{\|}}{P}}-Cl \qquad (III)$$

according to the following reaction:

$$(C_6H_5-CH_2O)_2-\overset{\overset{O}{\|}}{P}-R^1 + PCl_5 \longrightarrow$$

$$C_6H_5-CH_2O-\underset{\underset{Cl}{|}}{\overset{\overset{O}{\|}}{P}}-R^1 + C_6H_5-CH_2Cl + POCl_3$$

c) Coupling the Chloride of Formula (III) with a Peptide to Form the Protective Derivative of Formula:

$$R^1-\underset{\underset{OCH_2C_6H_5}{|}}{\overset{\overset{O}{\|}}{P}}-NH-CH_2-CO-R^2-N-\underset{\underset{R^3}{|}}{\overset{\overset{R^4}{|}}{CH}}-COOR^5 \qquad (IV)$$

in which $R^5$ is the protective group, such as the benzyl group and which corresponds to the following diagram:

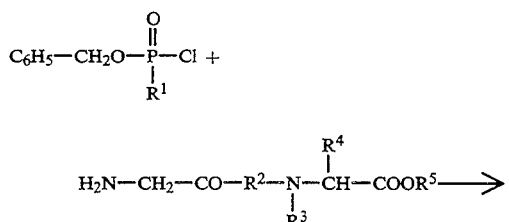

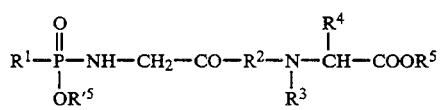

Derivative (IV) + HCl.

At the end of this stage, it is possible to carry out a deprotection of the derivative of formula (IV), e.g. by catalytic hydrogenation, optionally in the presence of lithium hydroxide or sodium bicarbonate, in order to obtain the derivative of formula (V)

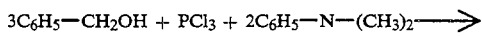
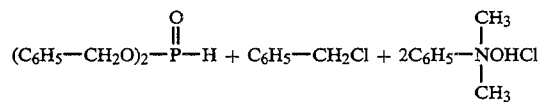

(V)

in which $R^5$ and $R'^5$ are H, Li or Na.

The dibenzyl phosphite used as the starting product in this process can be prepared from benzyl alcohol, $PCl_3$ and phenyl dimethyl amine by the following reaction:

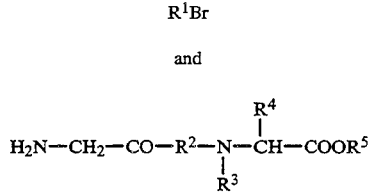

The compounds $R^1Br$ and

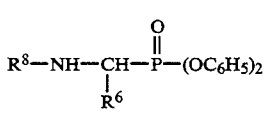

used respectively in stages a) and c) can also be prepared by conventional processes.

The peptide derivatives corresponding to the second embodiment of the invention in which $R^7$ is a single bond and $R^8$ a blocking group can be prepared by a process having the following successive stages:

a) synthesis of the compound of formula:

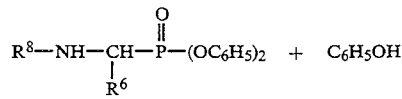

(VI)

by the following reaction:

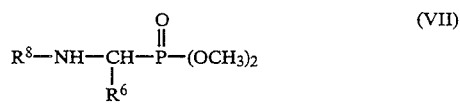

b) conversion of the compound of formula (VI) into the compound of formula:

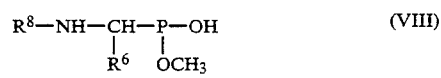

(VII)

by reaction with CH₃ONa according to the following diagram:

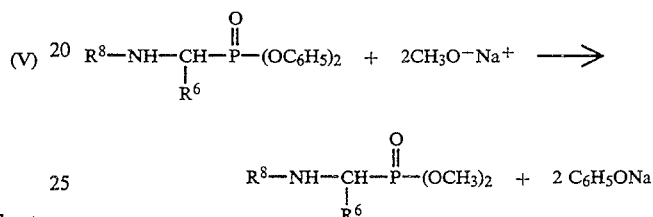

c) synthesis of the compound of formula:

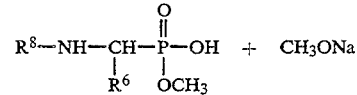

(VIII)

according to the following diagram

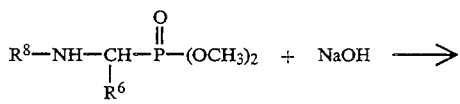

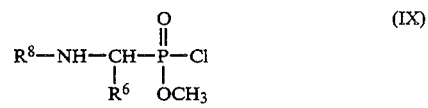

d) Synthesis of the Compound of Formula:

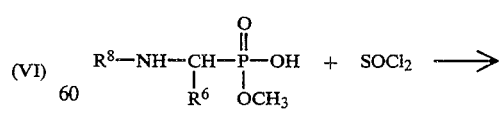

(IX)

by reaction of the product of formula (VIII) with $SOCl_2$ according to the following reaction diagram:

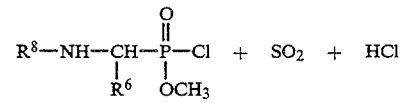

and then coupling the compound (IX) with a peptide of formula:

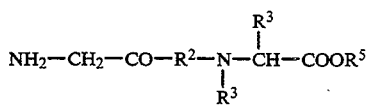

in which $R^5$ is an alkyl or aryl group to form the compound of formula:

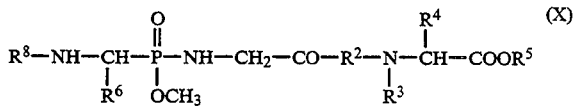

This can be followed by a deprotection of the derivative of formula (X), e.g. by catalytic hydrogenation as hereinbefore, in order to obtain the derivative of formula:

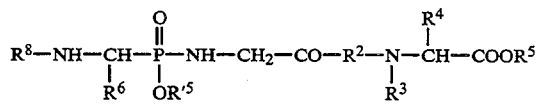

in which $R'^5$ is H, Na or Li.

The peptide derivatives corresponding to the second embodiment of the invention in which $R^7$ is a single bond and $R^8$ an optionally substituted aralkyl group, or in which $R^7$ is a derivative of an α-amino acid or a peptide and $R^8$ is an optionally substituted aralkyl group can be prepared by an analogous process having a supplementary stage for introducing $R^7$-$R^8$ or $R^8$.

In this case the same operating procedure is followed for preparing a peptide derivative of formula:

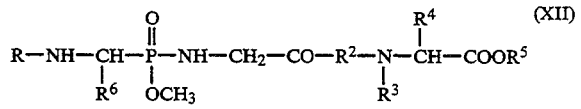

in which R is a protective group such as the benzyloxycarbonyl group and then the derivative of formula (XII) undergoes catalytic hydrogenation to form the derivative of formula:

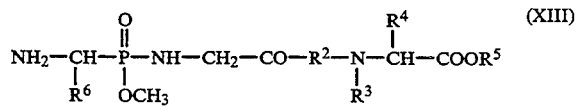

and the derivative of formula (XII) is reacted with $R^8$-$R^7$-OH to form the derivative of formula:

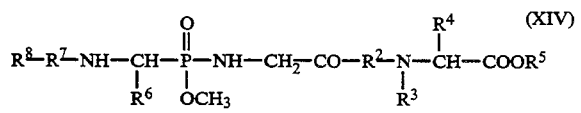

Finally, it is possible to carry out a deprotection of the derivative of formula (XIV) to obtain the derivative

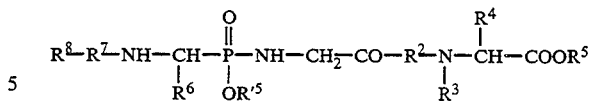

with $R'^5$ representing H, Na or Li.

The derivatives of peptides according to the invention have numerous applications due to their inhibiting power with respect to bacterial collagenases. They can be more particularly used in pharmaceutical compositions for the treatment of certain infections due to the presence of bacteria able to excrete collagenase, Thus, the presence of these bacteria can lead to a significant destruction of the collagen and consequently attack the integrity of the conjunctive tissue of the infected organism, This is in particular the case with infections by *Clostridium histolyticum* and *Pseudomonas aeruginosa*. The derivatives of peptides according to the invention can in particular be used for the treatment of periodontal illnesses associated with collagenolytic microorganisms responsible for the destruction of the collagen, e.g. occurring in the composition of the gums.

Thus, although the peptide derivatives according to the invention have no direct action on collagenolytic microorganisms. they constitute an interesting therapeutic means in certain pathologies (e.g. gangrene and dental infections), because they are powerful and specific inhibitors of bacterial collagenases. In these pharmaceutical applications, it is also possible to use the peptide derivatives according to the invention for inhibiting other metalloproteases having specificities close to those of bacterial collagenases involved in the metabolism of collagen.

Thus, the invention also relates to a pharmaceutical composition having a pharmaceutically effective quantity of a peptide derivative according to the invention and complying with formula (1), in which $R'^5$ is hydrogen or a metal. This composition can be in the form of a physiologically acceptable salt of the peptide derivative. In a vehicle or in an appropriate physiologically acceptable support. It can e.g. be administered in the form of solutions or suspensions by injection.

The preferred administration doses are 1 mg/kg/day to approximately 5 mg/kg/day.

The compositions can also be in the form of compositions intended for oral administration, such as tablets or capsules, e.g. obtained by combining the derivatives of peptides according to the invention with supports, excipients and additives of a conventional nature such as magnesium carbonate, magnesium stearate, talc. sugar, lactose, pectin, dextrin, starch, gelatin, tragacanth, methyl cellulose, sodium carboxymethyl cellulose, cacao butter, etc. Diluents, flayours, solubilizers, lubricants, suspending agents, binding agents, disintegrating agents, etc. can be added to the compositions. The active ingredients can also be encapsulated with other supports, etc.

The peptide derivatives according to the invention can also be used in other fields, e.g. for protecting skins and hides in the leather manufacturing field, as well as for the protection of gelatin in the different spheres using this product.

Thus, although the natural substrate of bacterial collagenases is mainly native collagen, it is known that this protease can use as the substrate collagen in its denatured form, i.e. gelatin. Gelatin is presently used in various contexts and it is of interest to maintain the perfect integrity of the gelatin for these applications. This can be obtained by using the peptide derivatives according to the invention as competitive inhibitors of bacterial collagenases able to destroy gelatin.

It is also possible to use the peptide derivatives according to the invention for isolating novel zinc proteases having a specificity close to that of bacterial collagenases, particularly within higher organisms. In this case, it is possible to use the inventive peptide derivatives as a ligand for producing affinity columns with 8 view to separating other zinc proteases.

It is also possible to use the peptide derivatives according to the invention for controlling the activity of bacterial collagenase, e.g. in biotechnological processes based on the use of collagenolytic bacteria, e.g. for tenderizing meat and the digestion of sediments in sedimentation tanks.

Other features and advantages of the invention can be gathered from reading the following examples given in an illustrative and non-limitative manner.

Among these examples, examples 1 to 5 illustrate the preparation of derivatives of peptides according to the first embodiment of the invention and examples 6 to 8 derivatives of peptides according to the second embodiment of the invention.

EXAMPLE 1

Preparation of the peptide derivative of formula desired dibenzylphenylethyl phosphonate is obtained with an 80% yield.

This product is then purified by flash chromatography on silica using as the eluent a mixture of ether and ethyl acetate in a volume ratio of 2:3. This gives the purified phosphonate with a 40% yield.

b) Preparation of the Monobenzyl Phenylethyl Phosphonate Chloride 1 mmole of phosphorus pentachloride in benzene is added to a solution in benzene of 1 mmole of dibenzylphenylethyl phosphonate, which has been previously obtained. The mixture is refluxed at 70° C. for 3 to 4h under an anhydrous atmosphere until the chloride is completely obtained. The benzene of said mixture is then evaporated and is taken up in dichloromethane. This solution is used immediately for carrying out coupling with the peptide.

c) Coupling with the Peptide

To the solution of 1 mmole of monobenzylphenylethyl phosphonate chloride in dichloromethane obtained previously is added at 0° C., 0.9 mmole of peptide HCl, Gly-Pro-Nle-OCH$_2$-C$_6$H$_5$ in dichloromethane and two equivalents of triethylamine. Reaction is allowed to take place, accompanied by stirring, for 30 minutes at 0° C. and then for a further 30 minutes at 250° C. The dichloromethane is then evaporated and the oil taken up in ethyl acetate, followed by washing with

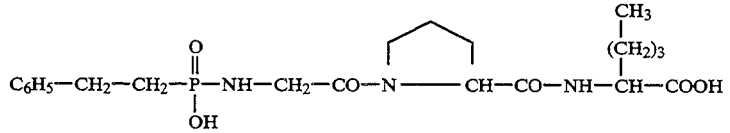

(compound n° 1)

This derivative is in accordance with formula (I), in which R$^1$ is the phenyl ethyl group, R$^2$ the proline derivative, R$^3$ a hydrogen atom, R$^4$ the n-butyl group and R$^5$ a hydrogen atom.

a) Preparation of the Dibenzyl Phenylethyl Phosphonate

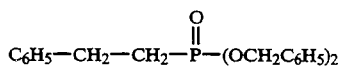

1 mmole of sodium hydride is carefully mixed in dimethyl formamide under a nitrogen atmosphere at −15° C. and to it is gradually added 1 mmole of dibenzyl phosphite dissolved in dimethyl formamide. The reaction is allowed to continue until all the hydrogen has been given off.

Then, accompanied by stirring, addition takes place of 1 mmole of phenylethyl bromide in dimethyl formamide, still under a nitrogen atmosphere and said addition takes place sufficiently slowly for the temperature to vary between −10° and 0° C. When all the phenylethyl bromide solution has been added, the reaction mixture is allowed to return to 25° C. The nitrogen is removed and stirring is maintained for 3h.

This dimethyl formamide (DMf) mixture is then evaporated under a high vacuum at 35° to 40° C., followed by taking up in ether. This is followed by washing the organic phase twice with water and drying on sodium sulphate. After evaporating the solvent, the water, 0.1N hydrochloric acid, 5% NaHCO$_3$ and then with water to neutrality. The organic phase is dried and then evaporated. This gives the protective peptide derivative with a yield of 90%. This derivative is purified by flash chromatography using as the elution solvent the dichloromethane methanol mixture (9:1 by volume).

d) Deprotection

The deprotection of the derivative is brought about by catalytic hydrogenation using palladium as the catalyst which gives compound no.1.

This compound is characterized by nuclear magnetic resonance of the phosphorus and the proton. In particular, the selective irradiation of the phosphorus makes it possible to identify in the proton spectrum of the product, the protons of the glycine residue and the phosphorus-substituting group R$^1$. These protons are scalar coupled to the phosphorus. The presence of such scalar couplings unambiguously demonstrates the existence of the phosphonamide bond between the glycine residue and the R$^1$ group substituting the phosphorus. The spectra were recorded at 500 MHz. The chemical displacements for the proton are expressed in ppm, taking as the reference tetramethyl silane (TMS). The data are represented as follows: chemical displacement (multiplicity, coupling constant in Hz).

The carbon 13 and phosphorus chemical displacements are respectively referenced at 85% relative to dioxan and H$_3$PO$_4$. The interpretation of the carbon 13 proton spectra was carried out by bidimensional proton-proton and proton-carbon 13 correlation methods.

The NMR characteristics are as follows: $^1$H NMR (D$_2$O): CH$_\epsilon$ $_{NLe}$ 0.88 (t,3, 7Hz); CH$\delta,\gamma$Nle 1.27–1,32(m,4); CH$\beta$Nle 1.65 (m,1); CH$\beta$Nle 1.76 (m,1); $\phi$-CH$_2$-CH$_2$ 1.88(m,2,$^{2j}$ HP16Hz); CH$\gamma$Pro 2(m,2); CH$\beta$Pro 2.05(m,1); CH$\beta$Pro 2.25(m,1); $\phi$-CH$_2$-CH$_2$2.82(m,2); CH$\delta$Pro 3.55(m,2); CH$\lambda$Gly 3.25–3.6-2(ABX, 2, $^3$JHP 9Hz, $^2$JAB 16 Hz); CH$\alpha$Nle-4.13(q,1)CH$\alpha$Pro4.40 (q,1); Ar 7.25–7.40(m,5). $^{13}$C NMR (D$_2$O): C$_{68}$Nle 14; C$\delta$Nle 22,5; C$\gamma$Pro 25.1; C$\gamma$Nle 28.1; C$\beta$ Pro 30.1; $\phi$-CH$_2$-CH$_2$3O.4; $\phi$-CH$_2$-CH$_2$ 31.5($^{1J}$CP 121 Hz); C$\beta$Nle 32.2; C$\alpha$Gly 44.2; C$\delta$Pro 47.6; C$\alpha$Nle 56.1; C$\alpha$Pro 61.5; CO Gly 172, CO Pro 174.3; CO Nle 144; Ar 129.5, 129. 126.9, 180. $^{31}$p NMR(D$_2$O): 28.3.

EXAMPLE 2

Preparation of the Peptide Derivative of Formula

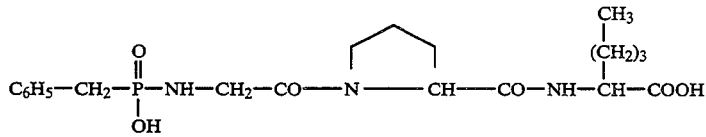

(compound n° 2)

Compound 2 corresponds to the peptide derivative of formula (1) in which R$^1$ is the phenylmethyl group, R$^2$ the derivative of proline, R$^3$ a hydrogen atom, R$^4$ the n-butyl group and R$^5$ a hydrogen atom.

The same operating procedure as in example 1 is followed in order to prepare said compound, except that in the first stage use is made of 1 mmole of phenylrnethyl bromide in place of 1 mmole of phenylethyl bromide.

The characteristics of the product obtained are as follows: $^1$H NMR (D$_2$O): CH$_\epsilon$ Nle 0.88 (t, 3.7 Hz); CH$\delta,\gamma$Nle 1.32 (m, 4); CH$\beta$Nle 1.65(m, 1); CH$\beta$ Nle 1.76 (m, 1); CH$\gamma$Pro 1.95(m, 2); CH$\beta$Pro 2.12 (m, 1); CH$\beta$Pro 2.25 (m, 1); $\phi$-CH$_2$3(m,2); CH$\delta$Pro 3.4(m,2); CH$\alpha$Gly 3.5–3.53(ABX,2, $^3$JHP7.2–8.05 Hz, $^2$JAB 16 Hz); CH$\beta$Nle 4.13 (q,1)CH$\alpha$Pro 4.40(q,1); Ar 7,25–7.40(m,5)-. $^{13}$C NMR (D$_2$O): C$_\epsilon$Nle 14; C$\delta$Nle 22.5: C$\gamma$Pro 25.1; C$\gamma$Nle 28.1; C$\beta$Pro 30,1; C$\beta$Nle 32.2 $\phi$-CH$_2$ 37,9-($^{1J}$CP 121 Hz); C$\alpha$Gly 44.2; C$\delta$Pro 47.6; C$\alpha$Nle 56.1; C$\alpha$ Pro 61.5; CO Gly 172, CO Pro 174.3; CO Nle 144; Ar 126.8, 129, 126.9, 180. $^{31}$p NMR(D$_2$O): 23.98.

EXAMPLE 3

Preparation of Compound No. 3 of Formula

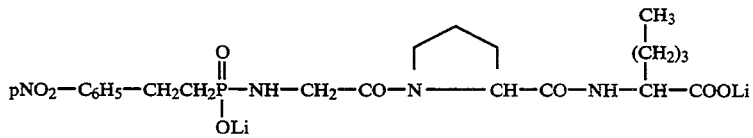

(compound n° 3)

This compound is in accordance with formula (!) in which R$^1$ is the p-nitrophenyl ethyl group, R$^2$ the proline derivative, R$^3$ a hydrogen atom, R$^4$ the n-butyl group and R$^5$ a lithium atom.

The same operating procedure as in example 1 is followed for preparing this compound, except that in the first stage use is made of 1 mmole of p-nitrophenylethyl bromide in place of 1 mmole of phenylethyl bromide.

In addition, in the final stage deprotection takes place of the derivative in the presence of lithium hydroxide, which leads to the lithium salt.

The characteristics of the product obtained are as follows: $^1$H NMR (D$_2$O): CH$_{68}$Nle 0.88 (t,3,7 Hz); CH$\delta,\gamma$Nle 1.27–1.32(m,4); CH$\beta$Nle 1.71 (m,1); CH$\beta$ Nle 1.80(m,1); NO$_2$-$\phi$-CH$_2$-CH$_2$ 1.92 (m,2, $^2$J HP 16 Hz); CH$\gamma$Pro 2.08(m,2); CH$\beta$Pro 2.18 (m, 1); CH$\beta$Pro 2.35 (m,1); NO$_2$-$\phi$-CH$_2$-CH$_2$ 2.95(m,2); CH$\delta$Pro 3.6(m,2); CH$\alpha$Gly 3.70–3.75(ABX,2, $^3$JHP 8 Hz, $^2$JAB 16 Hz); CH$\alpha$Nle 4.13(q,1)CH$\alpha$Pro 4.40 (q,1); Ar 7.25(d,2); 8.2 (d,2). $^{31}$p NMR (D$_2$O): 27.4.

EXAMPLE 4:

Preparation of the Peptide Derivative of Formula

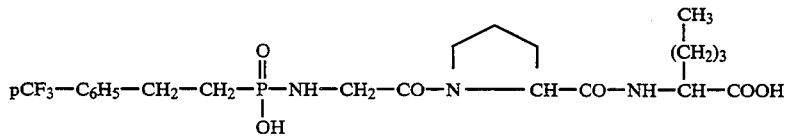

(compound n° 4)

This compound is a peptide derivative of formula (1) in which R$^1$ is the p-trifluorophenylethyl group, R$^2$ the proline derivative. R$^3$ a hydrogen atom, R$^4$ the n-butyl group and R$^5$ a hydrogen atom.

The same operating procedure as in example 1 is followed, except that use is made in the first stage of 1 mmole of p-trifluorophenylethyl bromide in place of 1 mmole of phenyl ethyl bromide.

The characteristics of the product obtained are as follows: $^1$H NMR(D$_2$O): CH$_\epsilon$Nle 0.88 (t,3); CH$\delta,\gamma$Nle 1.27–1.32-(m,4); CH$\beta$Nle 1.65(m,1).; CH$\beta$Nle 1.73(m, 1); CF$_3$-$\phi$-CH$_2$-CH$_2$-1.88(m,2, $^2$J HP 16 Hz); CH$\gamma$Pro 2 (m,2); CH$\beta$Pro 2.05(m, 1); CH$\beta$Pro 2.25(m,1); CF$_3$-$\phi$-CH$_2$-CH$_2$ 2.90 (m,2); CH$\delta$Pro 3.55(m,2); CH$\alpha$Gly 3.25–3.62(ABX, 2, $^3$JHP 9 Hz, $^2$JAB 16 Hz); CH$\alpha$Nle 4.13 (q,1)CH$\alpha$Pro 4.40 (q,1); Ar 7.33; 7,52; 7.63 (m, 4). $^{31}$p NNR (D$_2$O): 29.28.

COMPARATIVE EXAMPLE 1

Preparation of a Peptide Derivative in Accordance with Formula

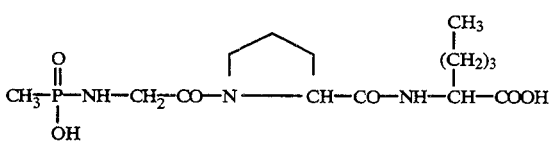

This compound is a peptide derivative of formula (I) in which $R^1$ is the methyl group, $R^2$ the proline derivative, $R^3$ a hydrogen atom, $R^4$ the n-butyl group and $R^5$ a hydrogen atom.

The same operating procedure as in example 1 is followed for preparing this compound, except that use is made in stage a) of 1 mmole of methyl bromide in place of 1 mmole of phenylethyl bromide. The characteristics of the product obtained are as follows: $^1$H NMR (D$_2$O): CH$_\epsilon$Nle 0.88 (t,3,); CH$_3$-P 1.25 (d, 3, $^{2J}$Hp 15 Hz); CH$\delta$,$\gamma$Nle 1.27–1.32 (m,4); CH$\beta$Nle 1.65 (m,1): CH$\beta$ Nle 1.76(m, 1); CH$\gamma$Pro 2(m,2); CH$\beta$Pro 2.05 (m, 1); CH$\beta$Pro 2.25 (m,1); CH$\delta$Pro 3.55 (m,2); CH$\alpha$Gly 3.7–3.73(ABX,2, $^3$JHP 8 Hz, $^2$JAB 16 Hz); CH$\alpha$Nlle 4.13 (q,1) CH$\alpha$Pro 4.40(q,1); Ar 7.25–7.40(m,5). $^{31}$p NNR(D$_2$O): 27.8.

EXAMPLE 5

Preparation of Compound No. 5 of Formula

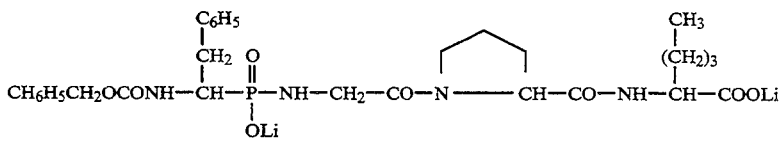

This compound is a peptide derivative of formula (i) in which $R^1$ is the group of formula:

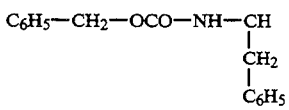

in which $R^2$ is the proline derivative, $R^3$ is H, $R^4$ is the n-butyl group and $R^5$ is Li.

a) Preparation of Benzyloxycarbonyl Phenylalanyl Dibenzyl Phosphonate.

To 15 ml of glacial acetic acid are added 26 ml (0.1 mole) of triphenyl phosphite, 15.1g (0.1 mole) of benzyl carbonate and 0.15 mole of benzyl aldehyde. The solution is then stirred for 1 hour at 25° C. and is then heated for a further hour at 80° C. Evaporation takes place under high vacuum at 100° C. followed by taking up in 150 ml of methanol and leaving at −40° C. After a few hours, a precipitate of the desired phosphonate is obtained with a 40 to 70% yield.

b) Preparation of Benzyloxycarbonyl Phenyl Alanyldimethyl Phosphonate

Very carefully 0.2 mole of solid sodium is diluted in 150 ml of methanol, followed by the addition of 10mmole of benzyloxycarbonyl phenyl alanyldibenzyl phosphonate previously obtained, dissolved in 50 ml of methanol. Stirring is continued at 25° C. for 2h, followed by evaporation, taking up in ether, washing with water, drying of the organic phase and evaporation. Leaving said oil at 4° C., a product which crystallizes is obtained. This product is purified by flash chromatography on silica using an ether-hexane mixture as the eluent.

c) Preparation of Benzyloxycarbonyl Phenyl Alanylmonomethyl Phosphonate 10 mmole of previously obtained benzyloxycarbonyl phenyl alanyldimethyl phosphonate are dissolved in 55 ml of methanol, followed by the addition of 20 mmole of NaOH. The solution is heated to boiling under reflux for 8h. This solution is then allowed to return to 25° C., accompanied by stirring for 8 to 12h. The solution is acidified with 2N HCl until a pH of 2 is obtained and then the methanol is evaporated in vacuo. The product is taken up in ethyl acetate, the organic phase dried and then evaporated. The product is crystallized in petroleum ether.

d) Coupling to the Peptide and Deprotection

Dilution takes place in dichloromethane of 1 mmole of benzyloxycarbonyl phenyl alanylmonomethyl phosphonate previously obtained and then 2 mmole of thionyl chloride are added. This solution is stirred for 4h at 25° C. Dry evaporation takes place under a high vacuum, dichloromethane is added again and evaporation takes place again. This is taken up in dichloromethane, followed by cooling at 0° C. and the addition of 1 mmole of Gly-Pro-Nle-OCH$_2$C$_6$H$_5$ hydrochloride and 2 mmole of triethylamine. Stirring is continued for 30 minutes at 0° C. and then for a further 30 minutes at 25° C.

The dichloromethane is evaporated and then the oil is taken up in ethyl acetate and washed with water, with 0.1N HCl, with 5% NaHCO$_3$ and then with water to neutrality. The organic phase is dried and then evaporated. This gives the protective derivative, which is purified by flash chromatography using as the elution solvent a dichloromethane-methanol mixture (:9:1 by volume). The derivative corresponds to the mixture of 4 diastereoisomers which can be separated into 4 fractions using a grafted silica column with a chiral group and using as the elution solvent a hexane-chloroform-n-propanol mixture.

Deprotection is then carried out as in example 1, but working in the presence of lithium hydroxide. Following deprotection, there is only a single asymmetrical centre at the phenyl alanyl group and consequently the 4 fractions can be distributed into two batches A and B.

Analysis by nuclear magnetic resonance of fraction A gave the following results: $^1$H NMR (D$_2$O): CH$_\epsilon$ Nle 0.88 (t,3,); CH$\delta$,$\gamma$Nle 1.32 (m,4); CH$\beta$Nle 1.65 (m,1); CH $\beta$Nle 1.76 (m,1); CH$\gamma$Pro 2(m,2); CH$\beta$Pro 2.05 (m, 1); CH$\beta$Pro 2.25 (m, 1); CH$\beta$ Phe 2.65 (m,1, $^{2J}\beta$ 14Hz, $^3$J $\alpha$B 12.6 Hz, $^{3J}$HP 6.3 Hz); CH$\delta$ Phe 3.19(m, 1, $^{2J}\beta\beta$14 Hz, $^{3J}\alpha\beta$ 3Hz, 3JHP 3 Hz; CH$\delta$ Pro 3.55 (m,2); CH$\alpha$ Gly 3.767–3.76 (ABX, 2, $^{3J}$HP 8 Hz $^{2J}$AB 16 Hz); CH$\alpha$ Phe 3.9. CH$\alpha$Nle 4.13 (q,1) CH$\alpha$Pro 4.40 (q,1);

φ-CH2-O 4.98–4.85(dd,2) Ar 7.25–7.40 (m,5). ³¹p NMR (D2O): 22.4.

EXAHPLE 6

Preparation of the Peptide Derivative of Formula

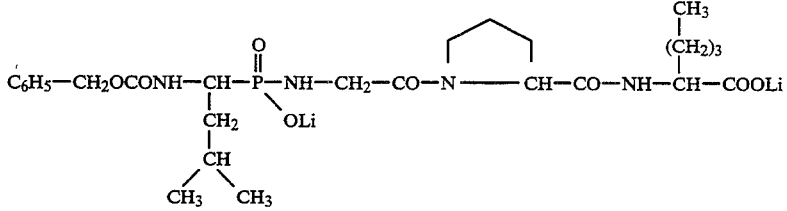
(compound n° 6)

This peptide derivative is in accordance with formula (1) in which R¹ represents the group of formula:

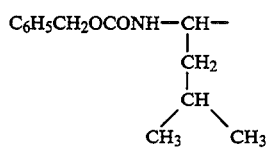

R² is the proline derivative, R³ a hydrogen atom, R⁴ the n-butyl group of leucine and R⁵ a hydrogen atom.

The same operating procedure as in example 5 is adopted for preparing said peptide derivative, except that in stage a) use is made of 0.15 mole of isobutyl aldehyde in place of 0.15 mole of benzyl aldehyde.

The characteristics of fraction A of the product obtained are as follows: ¹H NHR (D2O): CHε Nle 0.88 (t, 3,); CHδ,γNle 1.32 (m,4); CHβNle 1.65 (m, 1); CHβ Nle 1.76 (m, 1); CHδ Leu 1.2 (m, 1), CH3 Leu 0.88–0.91 (d, 3) CHγPro 2 (m, 2); CHβPro 2.05 (m, 1); CHβPro 2.25 (m, 1); CHβ Leu 1,54 (m, 1); CHβ Leu 1.67 (m, 1); CHδPro 3.55 (m, 2); CHαGly 3.767–3.76 (ABX, 2, ³JHP 8 Hz, ²JAB 16 Hz); CHα Leu 3.85; CHαNle 4.13 (q, 1) CHαPro 4.40 (q, 1); φ-CH2-O 4.98–4.85 (dd, 2) Ar 7.25–7.40 (m, 5).

EXAHPLE 7

Preparation of the Peptide Derivative of Formula

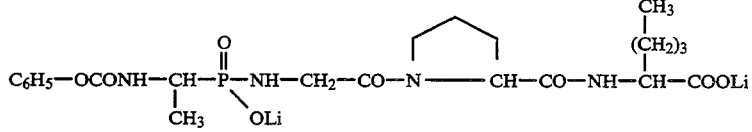
(compound n° 7)

This compound is a peptide derivative of formula (I) in which R¹ is the group of formula:

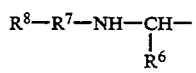

with R⁶ representing the methyl group, R⁷ being a single bond and R⁸ being the benzyloxycarbonyl group, R² the proline derivative, R³ a hydrogen atom, R⁴ the n-butyl group and R⁵ a hydrogen atom.

The same operating procedure as in example 5 is followed, except that 1 mmole of acetaldehyde is used in place of 1 rrrnole of benzylaldehyde.

The characteristics of fraction A of the product obtained are as follows: ¹H NNR (D2O): CHε Nle 0.88 (t, 3,); CHδ,γNle 1.32 (m,4); CHβNle 1.65 (m,1); CHβ Nle 1.76 (m,1); CH3 Ala 1.25 (d, 3); CHγPro 2(m, 2); CHβPro 2.05 (m, 1); CHβPro 2.25 (m, 1); CHδPro 3.55 (m,2); CHαGly 3.767–3.76(ABX, 2, ³JHP 8 Hz, ²JAB 16 Hz); CHα Ala 3.80; CHαNle 4.13 (q, 1) CHαPro 4.40 (q, 1); φ-CH2-O 4.98–4.85 (dd, 2) Ar 7.25–7.40 (m, 5).

EXAMPLE 8

In this example the activities of the compounds of examples 1 to 7 and comparative example 1 are measured by determining the inhibition constants of these compounds by the Henderson method in the case of compounds 1 to 4 and that of comparative example 1.

For compounds 5 to 7, the inhibition constant is determined on the basis of experimental values of the velocity constants Kon and Koff. The activity of the collagenase is followed by UV spectroscopy using as the chromogenic substrate Fa-Leu-Gly-Pro-Ala in a Tricine buffer at pH 6.8, 10 mMof CaCl2 at 250° C. and following the protocol described by Yotakis et al in Eur. J. Biochem., 160, pp.413–418, 1986 and *Clostridium Histolyticum collagenase* (EC 3.4.24.3). The results obtained with these different compounds are given in the following table.

It is clear from these results that the inhibition constants are much lower than in the case of the prior art compounds.

Thus, the best compound synthesized by Galardy has a constant Ki of $10^{-6}$M, whereas the best compound according to the invention has a constant Ki of $0.5 \cdot 10^{-9}$M, i.e. an activity gain by a factor of 1000.

TABLE

INHIBITION CONSTANTS OF CLOSTRIDIUM HISTOLYTICUM COLLAGENASE BY THE COMPOUNDS

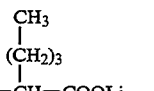

| Compound of Ex. | R¹ | R⁵ = R'⁵ | Ki ($10^{-9}$ M) |
|---|---|---|---|
| 1 | C6H5C2H4— | H | 45 |
| 2 | C6H5—CH2— | H | 360 |
| 3 | pNO2—C6H5—C2H4— | Li | 1 |
| 4 | pCF3—C6H5—C2H4— | H | 24 |
| Comparative ex. 1 | CH3 | H | 2600 |

TABLE-continued
INHIBITION CONSTANTS OF CLOSTRIDIUM HISTOLYTICUM COLLAGENASE BY THE COMPOUNDS $$R^1-\overset{O}{\underset{O}{\overset{\|}{P}}}-Gly-Pro-Nle-R^5$$

| Compound of Ex. | $R^1$ | $R^5 = R'^5$ | Ki $(10^{-9}$ M) |
|---|---|---|---|
| 5 | 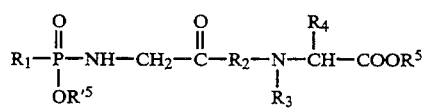 | Li | 0.5 |
| 6 | C$_6$H$_5$—CH$_2$OC(=O)—NH—CH—CH$_2$—CH(CH$_3$)$_2$ | Li | 10 |
| 7 | 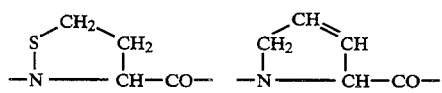 | Li | 25 |

We claim:

1. A peptide derivative having the formula:

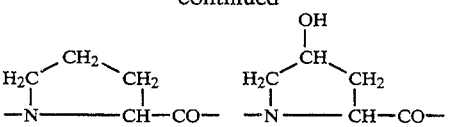

wherein:
— $R_1$ is selected from the group consisting of a phenylethyl group, a nitrophenylethyl group, a trifluoromethylphenylethyl group, and a group of the formula:
—CH($R^6$)-NH-$R^7$-$R^8$ in which $R^6$ is the side chain of ala, leu, or phe, and $R^7$ is a direct bond, and $R^8$ is an unsubstituted aralkyl group or a benzyloxycarbonyl group;
— $R^2$ is a divalent radical chosen from among proline, hydroxyproline, thiazolidine and dehydroproline of formulas:

connected by its N part to CO;
— $R^3$ is a hydrogen atom or a $C_1$-$C_4$ alkyl group;
— $R^4$ is the side chain of an aminoacid; and
— $R^5$ and $R'^5$ are a hydrogen atom or an alkali metal; and pharmaceutically acceptable metal salts thereof.

2. Peptide derivative according to claim 1 wherein $R_1$ is selected from the group consisting of a phenyethyl group, a nitrophenyethyl group, a trifluoromethylphenylethyl group, $R^2$ is the radical of the formula:

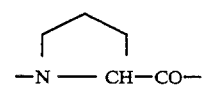

connected to CO by its N part, $R^3$ is a hydrogen atom and $R^4$ is n-butyl.

3. Peptide derivative according to claim 1 characterized in that $R^2$ is

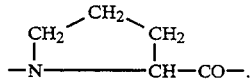

4. Peptide derivative according to claim 1 characterized in that $R^1$ is phenylethyl, $R^3$ is a hydrogen atom and $R^4$ is the n-butyl group.

5. Peptide derivative according to claim 1, characterized in that $R^1$ is the p-nitrophenylethyl or p-trifluoromethyl phenylethyl group.

6. Peptide derivative according to claim 1 characterized in that $R^3$ is a hydrogen atom and $R^4$ the n-butyl group.

7. Peptide derivative according to the formula:

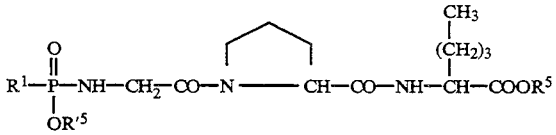

in which $R^1$ is the phenylethyl, p-nitrophenylethyl or p-trifluoromethyl phenylethyl group and $R^5$ and $R'^5$ are H or Li.

8. Peptide derivative according to claim 1, characterized in that it is in accordance with the formula:

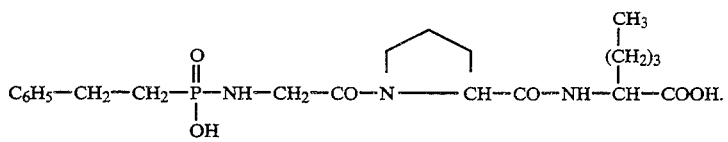

9. Peptide derivative according to claim 1, characterized in that it is in accordance with the formula:

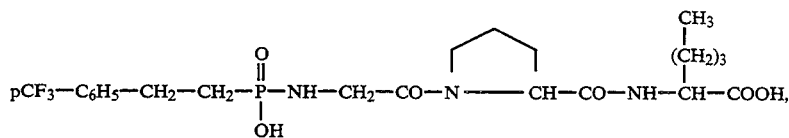

10. Peptide derivative according to claim 1 characterized in that it is in accordance with the formula:

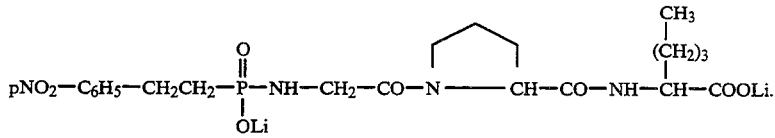

11. A peptide derivative according to claim 2 wherein $R^5$ represents a hydrogen, lithium or sodium atom.

12. A pharmaceutical composition characterized in that it comprises a peptide derivative according to claim 2 with $R^5$ representing a hydrogen atom or a pharmaceutically acceptable metal salt.

13. A method for treating bacterial infections in a living organism by administering to said organism a pharmaceutically effective quantity of peptide derivative as claimed in claim 1.

14. A method according to claim 13, in which the infection is by Clostridium histolyticum or Pseudomonas aeruginosa.

15. A peptide derivative having the formula:

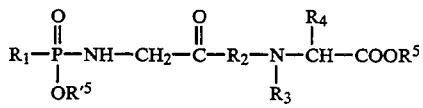

wherein:
— $R_1$ is the group of formula

—CH($R^6$)-NH-$R^7$-$R^8$ in which $R^6$ is the side chain of ala, leu, or phe, and $R^7$ is a direct bond, and $R^8$ is a benzyloxycarbonyl group:

— $R_2$ is a divalent radical chosen from among proline, hydroxyproline, thiazolidine and dehydroproline of formulas:

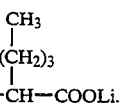

connected by its N part to CO;
— $R_3$ is a hydrogen atom or a $C_1$-$C_4$ alkyl group;
— $R_4$ is the side chain of an α-aminoacid; and
— $R^5$ and $R'^5$ are a hydrogen atom or an alkali metal; and pharmaceutically acceptable salts thereof.

16. A peptide derivative having the formula:

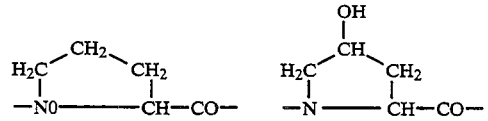

wherein:
— $R_1$ is the group of formula:

—CH($R^6$)-NH-$R^7$-$R^8$ in which $R^6$ is the side chain of ala, leu, or phe, and $R^7$ is a direct bond, and $R^8$ is an unsubstituted aralkyl group or a benzyloxycarbonyl group;

— $R_2$ is a divalent radical chosen from among proline, hydroxyproline, thiazolidine and dehydroproline of formula:

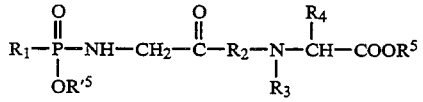

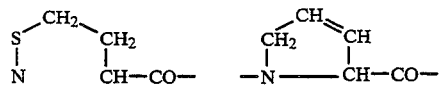

connected by its N part to CO;
— $R_3$ is a hydrogen atom or a $C_1$-$C_4$ alkyl group;
— $R_4$ is the side chain of an α-aminoacid; and
— $R^5$ and $R'^5$ are a hydrogen atom or an alkali metal; and pharmaceutically acceptable salts thereof.

17. A peptide derivative having the formula:

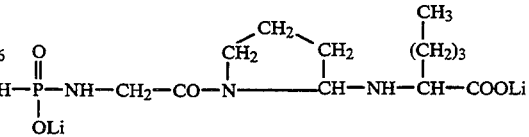

wherein $R_6$ is $CH_3$, -$CH_2$-$C_6H_5$ or -$CH_2$-CH($CH_3$)$_2$.

* * * * *

UNITED STATES PATENT AND TRADEMARK OFFICE
CERTIFICATE OF CORRECTION

PATENT NO. : 5,389,612
DATED : February 14, 1995
INVENTOR(S) : Vincent DIVE; Flavio TOMA; and Athanasios YIOTAKIS It is certified that error appears in the above-indentified patent and that said Letters Patent is hereby corrected as shown below:

Claim 15, Col. 22, lines 18-20, the left-hand formula should read as follows:

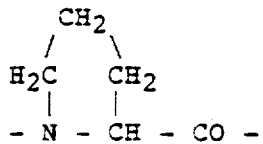

Claim 16, Col. 22, lines 51,53, the left-hand formula should read as follows:

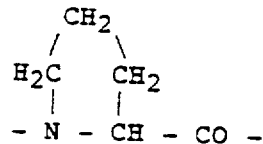

Signed and Sealed this

Nineteenth Day of December, 1995

Attest:

BRUCE LEHMAN

*Attesting Officer*  *Commissioner of Patents and Trademarks*